US012258611B2

(12) United States Patent
Kariatsumari (10) Patent No.: US 12,258,611 B2
(45) Date of Patent: Mar. 25, 2025

(54) DEVICE FOR DETECTING TOMATO PATHOGENIC FUNGUS AND DETECTION METHOD USING THE SAME (71) Applicant: Panasonic Intellectual Property Management Co., Ltd., Osaka (JP)

(72) Inventor: Yoshifumi Kariatsumari, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1055 days.

(21) Appl. No.: 17/092,377

(22) Filed: Nov. 9, 2020

(65) Prior Publication Data
US 2021/0062237 A1 Mar. 4, 2021

Related U.S. Application Data (63) Continuation of application No. PCT/JP2019/027291, filed on Jul. 10, 2019.

(30) Foreign Application Priority Data

Sep. 5, 2018 (JP) ................................. 2018-165960

(51) Int. Cl.
C12M 1/00 (2006.01)
C12M 1/12 (2006.01)
C12M 1/34 (2006.01)
C12M 3/00 (2006.01)
C12Q 1/04 (2006.01)

(52) U.S. Cl.
CPC ............... C12Q 1/04 (2013.01); C12M 25/04 (2013.01); C12M 41/46 (2013.01); *C12M 1/34* (2013.01)

(58) Field of Classification Search
CPC .................................. C12M 1/34; C12Q 1/04
See application file for complete search history.

(56) References Cited

U.S. PATENT DOCUMENTS

| 2004/0002126 | A1* | 1/2004 | Houde | G01N 33/54366 435/7.32 |
| 2009/0297571 | A1* | 12/2009 | Cornish | A01N 43/36 514/383 |
| 2013/0334042 | A1* | 12/2013 | Grieve | C12Q 1/005 204/403.01 |

(Continued)

FOREIGN PATENT DOCUMENTS

| CN | 111836879 A | 10/2020 |
| CN | 111836881 A | 10/2020 |

(Continued)

OTHER PUBLICATIONS

The Extended European Search Report dated Oct. 1, 2021 for the related European Patent Application No. 19857667.0.

(Continued)

*Primary Examiner* — Nathan A Bowers
(74) *Attorney, Agent, or Firm* — Rimon P.C.

(57) ABSTRACT

The present disclosure provides a device for detecting a tomato pathogenic fungus, the device including an artificial cell wall, a test-sample-solution receptacle disposed over the artificial cell wall, and a culture-solution storage disposed under the artificial cell wall, wherein, in the culture-solution storage, a culture solution contains greater than or equal to 0.5 mg/L and less than or equal to 1.3 mg/L of fludioxonil.

1 Claim, 4 Drawing Sheets (56) References Cited

U.S. PATENT DOCUMENTS

| | | | |
|---|---|---|---|
| 2017/0037444 | A1 | 2/2017 | Uriu |
| 2019/0048388 | A1 | 2/2019 | Yamaguchi et al. |
| 2019/0264250 | A1 | 8/2019 | Uriu |
| 2021/0040531 | A1 | 2/2021 | Ishidou et al. |
| 2021/0040532 | A1 | 2/2021 | Yamaguchi et al. |

FOREIGN PATENT DOCUMENTS

| | | |
|---|---|---|
| JP | 2005-287337 | 10/2005 |
| JP | 6167309 B | 7/2017 |
| JP | 2020-005572 A | 1/2020 |
| KR | 10-2018-054000 A | 5/2018 |
| WO | 2018/011835 A1 | 1/2018 |
| WO | 2018/138935 | 8/2018 |

OTHER PUBLICATIONS

International Search Report of PCT application No. PCT/JP2019/027291 dated Oct. 15, 2019.

Paul F. Morris et al., "Chemotropic and Contact Responses of Phytophthora sojae Hyphae to Soybean Isoflavonoids and Artificial Substrates", Plant Physiol. (1998) 117: 1171-1178.

Hirofumi Suzuki et al., "Efficacy of fungicides in controlling Botrytis cinerea", Ann. Rept. Kansai Pl. Prot. (53): 13-19 (2011), with English Summary.

Misa Maeda et al., "Screening of effective fungicides against leaf spot on tomato caused by Stemphylium lycopersici", Kyushu Pl. Prot. Res. 50:10-13 (2004).

English Translation of Chinese Search Report dated Oct. 31, 2023 for the related Chinese Patent Application No. 201980030504.9.

\* cited by examiner

DEVICE FOR DETECTING TOMATO PATHOGENIC FUNGUS AND DETECTION METHOD USING THE SAME

BACKGROUND

1. Technical Field

The present disclosure relates to a device for detecting a tomato pathogenic fungus and a selective detection method using the device.

2. Description of the Related Art

The plant pathogenic fungi have a characteristic feature of invading plants by, for example, forming appressoria to adhere to the surfaces of plants, and subsequently looking for pores such as stoma tissues and spreading hyphae through the pores into the plant bodies, or releasing plant-cell-wall degrading enzymes (cellulase and pectinase) from hyphae.

This is utilized in, for example, as disclosed in Japanese Unexamined Patent Application Publication No. 2005-287337, a method of measuring fungi using a fine-porous-membrane support. In addition, Paul F. Morris. et. al. "Chemotropic and Contact Responses of *Phytophthora sojae* Hyphae to Soybean Isoflavonoids and Artificial Substrates", Plant Physiol. (1998) 117: 1171-1178 discloses that one species of plant pathogenic *Oomycota*, *Phytophthora sojae*, spreads pseudohyphae to grow not horizontally but downwardly as if sinking, and to penetrate a PET (polyethylene terephthalate) membrane having 3 μm pores.

The present inventors focused on this feature and have already proposed a method for detecting plant pathogenic *Oomycota* (Japanese Patent No. 6167309).

SUMMARY

The present disclosure is directed to a plant, tomato, which often suffers from fungus diseases that are said to be mostly caused by three species of pathogenic fungi: a tomato gray mold fungus (*Botrytis cinerea*), a tomato Cercospora leaf mold fungus (*Pseudocercospora fuligena*), and a tomato leaf mold fungus (*Passalora fulva*). Of these pathogenic fungi, the gray mold fungus (*Botrytis cinerea*) is omnivorous and infects other plants, whereas the Cercospora leaf mold fungus (*Pseudocercospora fuligena*) and the leaf mold fungus (*Passalora fulva*) have been known to infect tomato alone and are highly plant-specific pathogenic fungi. For these pathogenic fungi specific to tomato, the present inventors considered that such a tomato pathogenic fungus needs to be detected at a stage of not knowing which fungus is actually present on tomato leaves, namely, the pre-onset stage, and performed studies.

On the other hand, the basic technique of selectively detecting a fungus described in Japanese Patent No. 6167309 and used by the present inventors, that is, the technique of distinguishing a pathogenic fungus using an artificial cell wall can detect, in addition to tomato pathogenic fungi, other plant pathogenic fungi. Specifically, when a pathogenic fungus for another plant adheres to tomato leaves, it may be detected as a tomato pathogenic fungus. Tomato is mostly cultivated not from seeds but from seedlings; in the seedling fields, for example, tomato may be cultivated together with other plants, or the same facility may be repeatedly used for a plurality of plants, so that plant pathogenic fungi other than tomato pathogenic fungi may adhere to tomato seedlings. In addition, as in the seedling fields, in the actual cultivation sites and cultivation facilities such as plastic greenhouses, pathogenic fungi for plants other than tomato may adhere to tomato seedlings. When this is not addressed, plant pathogenic fungi other than tomato pathogenic fungi may give false positives in the technique of distinguishing a pathogenic fungus using an artificial cell wall, which may result in considerable disadvantages in cultivation, such as unnecessary use of chemicals and introduction of new seedlings.

This probability of giving false positives was studied and investigated, and some fungi other than tomato pathogenic fungi were actually found to give false positives in a detection method using an artificial cell wall under development. These were four species that are *Biscogniauxia* fungi, *Penicillium* fungi, *Phoma* fungi, and *Trichoderma* fungi. Thus, studies on how not to detect these became necessary.

Under such circumstances, the present disclosure has been made. One non-limiting and exemplary embodiment provides a selective detection device and a detection method for a tomato pathogenic fungus.

The present inventors performed thorough studies and, as a result, found that a detection device having a configuration described below can achieve the above-described object; and the inventors further performed studies on the basis of such findings and have completed the present disclosure.

In one general aspect, the techniques disclosed here feature a device for detecting a tomato pathogenic fungus, the device including an artificial cell wall, a test-sample-solution receptacle disposed over the artificial cell wall, and a culture-solution storage disposed under the artificial cell wall, wherein, in the culture-solution storage, a culture solution contains greater than or equal to 0.5 mg/L and less than or equal to 1.3 mg/L of fludioxonil.

The present disclosure provides a device and a method for simply and safely achieving selective detection of a tomato pathogenic fungus. The present disclosure achieves detection of the presence of a tomato pathogenic fungus at the stage prior to onset caused by the fungus. In this case, false positives due to non-tomato plant pathogenic fungi are prevented, which is highly advantageous in industrial applicability.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Hereinafter, embodiments according to the present disclosure will be specifically described. However, the present disclosure is not limited to these.

Figure 1:
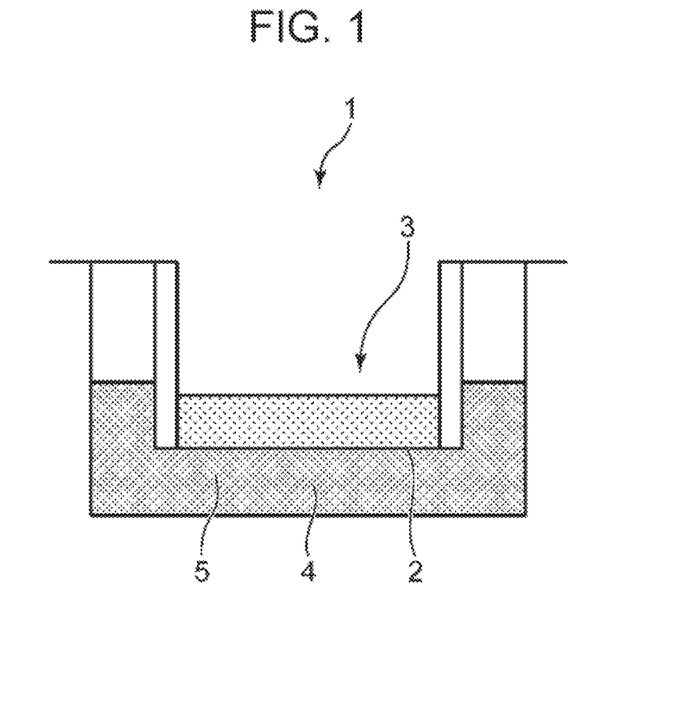
FIG. 1 is a schematic sectional view of an example of a detection device according to this embodiment.

As illustrated in FIG. 1, a device 1 for detecting a tomato pathogenic fungus according to this embodiment includes an artificial cell wall 2, a test-sample-solution receptacle 3 disposed over the artificial cell wall 2, and a culture-solution storage 4 disposed under the artificial cell wall 2, wherein, in the culture-solution storage 4, a culture solution 5 contains greater than or equal to 0.5 mg/L and less than or equal to 1.3 mg/L of fludioxonil.

The test-sample-solution receptacle 3 is a container for receiving a test sample solution, and the container desirably has, at the upper end, a flange. The bottom surface of the test-sample-solution receptacle 3 is formed of the artificial cell wall 2.

Figure 2:
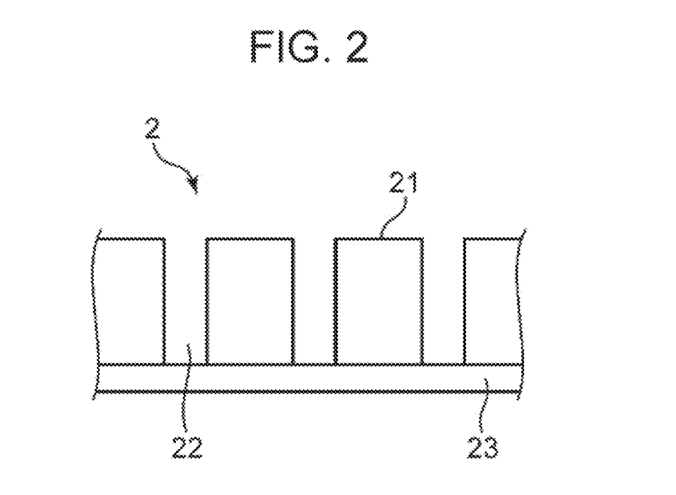
FIG. 2 is a schematic sectional view of an example of an artificial cell wall in a detection device according to this embodiment.

As illustrated in FIG. 2, the artificial cell wall 2 preferably includes at least a substrate 21 having through-holes 22 and a cellulose membrane 23 disposed on one of the surfaces of the substrate 21. Use of such an artificial cell wall facilitates selective detection of the target tomato pathogenic fungus.

The through-holes 22 extend from the front surface to the back surface of the substrate 21. The through-holes preferably have a hole diameter of greater than or equal to 2 μm and less than or equal to 7 μm (cross section: greater than or equal to 4.5 μm$^2$ and less than or equal to 38.5 μm$^2$). When the hole diameter is in such a range, the target pathogenic fungus can be selectively detected with more certainty.

In order to selectively detect the target pathogenic fungus with more certainty, the thickness of the cellulose membrane 23 is also preferably adjusted. Specifically, the cellulose membrane 23 preferably has a thickness of greater than or equal to 0.5 μm and less than or equal to 2 μm.

In the artificial cell wall 2 according to this embodiment, the hole diameters of the through-holes 22 of the substrate 21 and the thickness of the cellulose membrane 23 are adjusted so as to satisfy the above-described ranges; since most of tomato non-pathogenic fungi do not penetrate the cellulose membrane 23, some of tomato non-pathogenic fungi are inferentially excluded at this stage. On the other hand, tomato pathogenic fungi that are targets in this embodiment distinctively appear on the back surface of the substrate.

The thickness of the substrate 21 is not particularly limited, and is preferably, for example, about 5 to about 150 μm.

As illustrated in FIG. 1, into the test-sample-solution receptacle 3, a test sample solution is supplied. When this test sample solution contains a tomato pathogenic fungus, the tomato pathogenic fungus is placed on the front surface of the substrate 21.

In this embodiment, the test sample solution is a solution mainly containing fungi adhering to tomato leaves (fungus collected solution), and is not particularly limited as long as it is a liquid that may contain a target pathogenic fungus. Examples include a liquid having been used for washing tomato leaves, and a liquid in which tomato leaves have been immersed, for example, water, physiological saline, and surfactant-containing water (Tween 80: 0.01 to 0.1%).

The tomato pathogenic fungus that is the target of the detection device according to this embodiment is preferably at least one selected from the group consisting of a tomato gray mold fungus (*Botrytis cinerea*), a tomato Cercospora leaf mold fungus (*Pseudocercospora fuligena*), and a tomato leaf mold fungus (*Passalora fulva*).

The detection device according to this embodiment preferably does not detect fungi that may be present on tomato leaves, but are tomato non-pathogenic fungi such as *Biscogniauxia* fungi, *Penicillium* fungi, *Phoma* fungi, and *Trichoderma* fungi. More specifically, the tomato non-pathogenic fungi are *Biscogniauxia maritima, Penicillium olsonii, Phoma multirostrata*, and *Trichoderma asperellum*.

Incidentally, in this Description, the term "tomato pathogenic" means having pathogenicity to tomato. The term "tomato non-pathogenic" means not having pathogenicity to tomato. Even when a fungus has pathogenicity, as long as it does not have pathogenicity to tomato, the fungus is "tomato non-pathogenic". Stated another way, as long as the fungus does not adversely affect tomato, the fungus is "tomato non-pathogenic". The prefix "non" included in the term "tomato non-pathogenic" does not modify "tomato", and the prefix "non" modifies "pathogenic".

In the detection device according to this embodiment, the culture-solution storage 4 disposed under the artificial cell wall 2 contains the culture solution 5. The culture solution 5 is not particularly limited as long as it is a culture solution for culturing the fungus, and may be a commonly used culture medium or culture solution. For example, commonly used culture media for culturing fungi that are potato dextrose media and Sabouraud dextrose media can be used. Incidentally, in order to accelerate culture of the fungus, the culture solution may be added not only to the culture-solution storage 4 but also to the test sample solution.

In this embodiment, it is important that the culture solution 5 contains greater than or equal to 0.5 mg/L and less than or equal to 1.3 mg/L of fludioxonil. This feature enables, in detection of a pathogenic fungus, exclusion of interfering fungi that give false positives (tomato non-pathogenic fungi), which enables selective detection of the target tomato pathogenic fungus.

In this embodiment, fludioxonil (Fludioxonil), which is added to the culture solution (culture medium) in the culture-solution storage in order to selectively detect a tomato pathogenic fungus adhering leaves, is a phenylpyrrole-based non-systemic fungicide. Fludioxonil is a compound and agricultural chemical substance that inferentially acts on the plasma membranes of filamentous fungi to affect their permeability to substances and to inhibit uptake of amino acids and glucose into the cells, to thereby exert antifungal action.

In the culture solution, when the amount of fludioxonil is less than 0.5 mg/L, tomato non-pathogenic fungi other than the target tomato pathogenic fungus may be detected, so that tomato non-pathogenic fungi interfering detection of the tomato pathogenic fungus may not be completely excluded. Alternatively, in the culture solution, when the amount of fludioxonil is greater than 1.3 mg/L, a portion of or even the entirety of the target tomato pathogenic fungus may be excluded.

Figure 3:
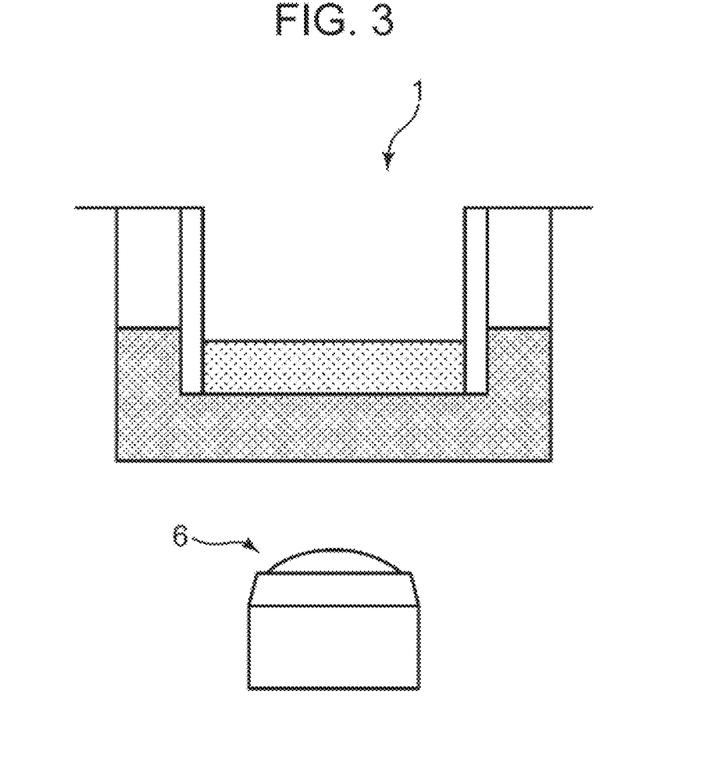
FIG. 3 is a schematic sectional view of an example of a detection device according to this embodiment.
Figure 4:
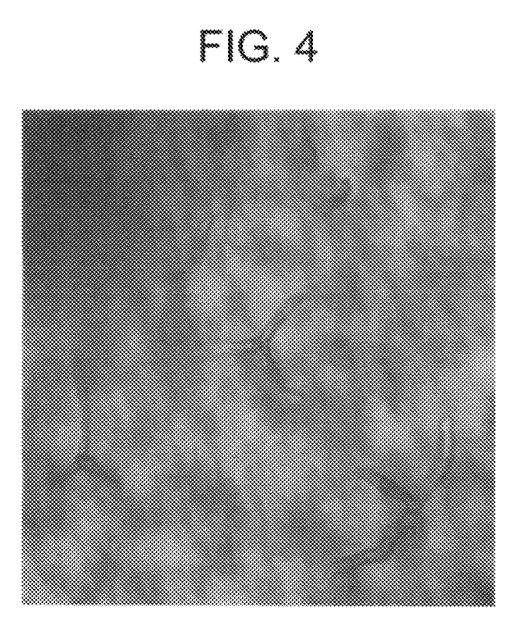
FIG. 4 is a micrograph of the back surface of an artificial cell wall in which a tomato gray mold fungus (*Botrytis cinerea*) penetrates the artificial cell wall.

In the detection device according to this embodiment, after the lapse of a certain culture period, observation of the back surface of the cellulose membrane 23 of the artificial cell wall 2 is performed as to whether or not the tomato pathogenic fungus appears, to thereby determine the presence or absence of the tomato pathogenic fungus in the sample. How to perform the observation is not particularly limited; for example, as illustrated in FIG. 3, a microscope 6 may be disposed below the artificial cell wall 2, and the microscope 6 may be used to perform optical observation.

The culture period of the fungus is not particularly limited, but is preferably longer than or equal to 72 hours. The culture temperature is preferably about 20 to about 28° C.

The present disclosure further encompasses a method for detecting a tomato pathogenic fungus, the method including using the above-described detection device to selectively detect a tomato pathogenic fungus.

The method for detecting a tomato pathogenic fungus according to this embodiment is not particularly limited in terms of the other steps as long as the above-described detection device is used; for example, the method includes a step of introducing a test sample solution into the test-sample-solution receptacle 3 of the detection device; a step of leaving the test sample solution under static conditions within the detection device (culture step); a step of, after the leaving under static conditions, observing the back surface of the artificial cell wall 2 (cellulose membrane 23) of the detection device; and a step of, in the case where the observation reveals the presence of the fungus at the back surface of the cellulose membrane 23, determining that the test sample solution contains the tomato pathogenic fungus.

This Description discloses techniques of various modes as described above; of these, main techniques are summarized as follows.

A device for detecting a tomato pathogenic fungus according to an aspect of the present disclosure includes an artificial cell wall, a test-sample-solution receptacle disposed over the artificial cell wall, and a culture-solution storage disposed under the artificial cell wall, wherein, in the culture-solution storage, a culture solution contains greater than or equal to 0.5 mg/L and less than or equal to 1.3 mg/L of fludioxonil.

Such a configuration provides a device and a method for simply and safely achieving selective detection of a tomato pathogenic fungus.

In the detection device, preferably, the artificial cell wall at least includes a substrate that has through-holes having a hole diameter of greater than or equal to 2 µm and less than or equal to 7 µm and that has a thickness of greater than or equal to 5 µm and less than or equal to 150 µm, and a cellulose membrane disposed on one of surfaces of the substrate and having a thickness of greater than or equal to 0.5 µm and less than or equal to 2 µm. In this case, the above-described advantages are inferentially provided with more certainty.

In the detection device, preferably, the tomato pathogenic fungus to be detected is at least one selected from the group consisting of a tomato gray mold fungus (*Botrytis cinerea*), a tomato Cercospora leaf mold fungus (*Pseudocercospora fuligena*), and a tomato leaf mold fungus (*Passalora fulva*). In this case, the above-described advantages are inferentially further provided.

The detection device preferably does not detect tomato non-pathogenic fungi that may be present on tomato leaves and that are *Biscogniauxia* fungi, *Penicillium* fungi, *Phoma* fungi, and *Trichoderma* fungi. In this case, the above-described advantages are inferentially further provided.

The tomato non-pathogenic fungi more preferably include *Biscogniauxia maritima*, *Penicillium olsonii*, *Phoma multirostrata*, and *Trichoderma asperellum*.

A method for detecting a tomato pathogenic fungus according to another aspect of the present disclosure includes using the detection device to selectively detect a tomato pathogenic fungus.

Hereinafter, the present disclosure will be more specifically described with reference to Examples. However, the scope of the present disclosure is not limited to these.

EXAMPLES

Preparation of Fungi

Culture of *Botrytis cinerea*

*Botrytis cinerea*, which is one of tomato pathogens and is a pathogenic fungus that causes tomato gray mold, was inoculated onto a potato dextrose agar medium (Difco™ Potato Dextrose Agar). Subsequently, the medium was left static at a temperature of 25° C. for a week. The *Botrytis cinerea* was given by Associate Professor Shimizu, Faculty of Applied Biological Sciences, Gifu University. Subsequently, the potato dextrose agar medium having cultured *Botrytis cinerea* with sufficient hyphal growth was left under irradiation with black light for four days or longer, and subsequently left in a room-temperature environment for two weeks or longer, to promote sporulation. To the resultant potato dextrose agar medium having cultured *Botrytis cinerea*, several milliliters of sterile pure water was dropped, and the surface of the hyphae was rubbed with, for example, a platinum loop or a brush, to obtain a disintegrated hypha-spore mixed suspension.

Culture of *Pseudocercospora fuligena*

*Pseudocercospora fuligena*, which is one of tomato pathogens and is a pathogenic fungus that causes tomato Cercospora leaf mold, was inoculated onto a potato dextrose agar medium. Subsequently, the medium was left static at a temperature of 28° C. for a week. *Pseudocercospora fuligena* was distributed by The Genetic Resources Center, The National Agriculture and Food Research Organization (MAFF No. 306728). Subsequently, hyphae of *Pseudocercospora fuligena* were transferred from the potato dextrose agar medium to a burdock root powder agar medium, further left static for one to two weeks at a temperature of 28° C.; after hyphae sufficiently grew again, the surface of the hyphae was subjected to a mechanical stress such as rubbing with, for example, a platinum loop or a brush; subsequently, the medium was left under irradiation with black light for four days or longer, subsequently left in a room-temperature environment for two weeks or longer, to promote sporulation again. To the resultant burdock root powder agar medium having cultured *Pseudocercospora fuligena*, several milliliters of sterile pure water was dropped, and the surface of the hyphae was rubbed with, for example, a platinum loop or a brush, to obtain a disintegrated hypha-spore mixed suspension.

Culture of *Passalora fulva*

*Passalora fulva*, which is one of tomato pathogens and is a pathogenic fungus that causes tomato leaf mold, was inoculated onto a potato dextrose agar medium. Subsequently, the medium was left static at a temperature of 23° C. for one to two weeks. *Passalora fulva* was distributed by The Genetic Resources Center, The National Agriculture and Food Research Organization (MAFF No. 726744).

Subsequently, to the potato dextrose agar medium having cultured *Passalora fulva* with sufficient hyphal growth, several milliliters of sterile pure water was dropped, and the surface of the hyphae was rubbed with, for example, a platinum loop or a brush, to obtain a disintegrated hypha-spore mixed suspension.

Culture of *Biscogniauxia maritima, Penicillium olsonii, Phoma multirostrata*, and *Trichoderma asperellum*

*Biscogniauxia maritima, Penicillium olsonii, Phoma multirostrata*, and *Trichoderma asperellum*, which are not tomato pathogens but were present on tomato leaves, were sampled from the tomato leaves, isolated, and then inoculated onto a potato dextrose agar medium. The tomato plants serving as the isolation sources were sampled at a plurality of sites. The isolation method was as follows: into a clean resin container or resin bag, several tomato leaves sampled were placed together with a fungus collection solution composed of physiological saline containing 0.1% surfactant Tween 80 (SIGMA-ALDRICH), and stirred for 1 minute to transfer the fungi adhering to the leaves to the fungus collection solution; this fungus collection solution was diluted, and applied to a potato dextrose agar medium containing 100 mg/L of streptomycin sulfate (Wako) by the spread plate culture technique; subsequently, the medium was incubated at 25° C. for several days and, from the produced fungus colonies, the isolation was performed. We requested Tama Laboratory, (general incorporated association) Japan Food Research Laboratories to perform identification. The above-described *Biscogniauxia maritima, Penicillium olsonii, Phoma multirostrata*, and *Trichoderma asperellum* isolated and then inoculated onto the potato dextrose agar medium were left static at a temperature of 25° C. for a week. Subsequently, to the potato dextrose agar medium on which the four species of fungi were cultured with sufficient hyphal growth or sufficient sporulation, several milliliters of sterile pure water was dropped; the surface of the hyphae was rubbed with, for example, a platinum loop or a brush, to obtain a disintegrated hypha-spore mixed suspension.

Preparation of Artificial Cell Wall

The artificial cell wall in the detection device was prepared in the following manner.

First, cellulose (SIGMA-ALDRICH, trade name: Avicel PH-101) was dissolved in an ionic liquid, to prepare a cellulose solution having a concentration of 1%. The ionic liquid was 1-Butyl-3-methyl imidazolium chloride (manufactured by SIGMA-ALDRICH). The cellulose solution was heated at 60° C. Subsequently, the cellulose solution was applied by spin coating to the back surface of a container having, at the bottom surface, a polyethylene terephthalate film (Millipore, trade name: Millicell PISP 12R 48) for 30 seconds at a revolution rate of 2000 rpm. The polyethylene terephthalate film functioned as the substrate 21 in the artificial cell wall in FIG. 2, and had a plurality of through-holes having a diameter of 3 μm and randomly arranged. In this way, a cellulose membrane was formed on the back surface of the polyethylene terephthalate film so as to have a thickness of 0.5 μm.

The container having, at the bottom surface, the polyethylene terephthalate film on the back surface of which the cellulose membrane was formed, was left to stand in ethanol for 12 hours at room temperature. In this way, 1-Butyl-3-methyl imidazolium chloride was replaced and removed by ethanol, and then finally drying was performed within a vacuum desiccator. Thus, such artificial cell walls were provided for being used in Examples and Comparative Examples.

Preparation of Device for Detecting Tomato Pathogenic Fungus

The above-described container having, at the bottom surface, the artificial cell wall including the polyethylene terephthalate film (substrate) having, on its back surface, the cellulose membrane was placed on a culture medium container (culture-solution storage), to provide a device for detecting a tomato pathogenic fungus. The culture medium container was a 24-well flat-bottom culture plate (Corning Incorporated, trade name: 24 Well Cell Culture Cluster Flat Bottom). Between the culture medium container and the artificial-cell-wall-formed container, 600 μL of a liquid culture medium (culture solution) was charged so as to be in contact with the back surface of the artificial-cell-wall-formed container. The liquid culture medium was a dilute potato dextrose liquid culture medium (Difco (registered trademark) 2.4 g/L aqueous solution of Potato Dextrose Broth) prepared by adding a 1.3% DMSO (SIGMA) solution of a compound fludioxonil (Fludioxonil, manufactured by SIGMA-ALDRICH) such that the fludioxonil concentration became 0.5 mg/L in Example 1 and 1.3 mg/L in Example 2. In Comparative Example 1, the preparation was performed by adding the 1.3% DMSO solution of fludioxonil such that the fludioxonil concentration became 133 mg/L.

Furthermore, in Comparative Example 2, the preparation was performed by adding the 1.3% DMSO solution of fludioxonil such that the fludioxonil concentrations became 0.1, 0.5, 1.3, 5.3, and 13 mg/L.

Examples 1-2 and Comparative Examples 1-2

In Examples 1-2 and Comparative Example 1, into the artificial-cell-wall-formed container, 200 disintegrated hypha-spore mixed suspensions containing hyphal fragments and spores of *Botrytis cinerea, Pseudocercospora fuligena, Passalora fulva, Biscogniauxia maritima, Penicillium olsonii, Phoma multirostrata*, and *Trichoderma asperellum* were individually added, and sterile purified water was added to each of the disintegrated hypha-spore mixed suspensions such that the total volume became 200 μL, to prepare test sample solutions. On the other hand, in Comparative Example 2, test sample solutions were prepared as in Example 1 except that 200 disintegrated hypha-spore mixed suspensions containing *Trichoderma asperellum* were added.

Subsequently, sterile purified water was added such that the total volume with such a disintegrated hypha-spore mixed suspension became 200 μL. The tomato-pathogenic-fungus selection method device in which the seven species of fungi were added was left to stand at a temperature of 25° C. for 72 hours, and the number of hyphae penetrating the artificial cell wall and observed at the back surface was visually counted using an optical microscope. An example of the photographs observed with the optical microscope (tomato gray mold fungus (*Botrytis cinerea*)) is illustrated in FIG. 4.

Discussions

The results of Example 1 are illustrated in FIG. 5. The results of Example 2 are illustrated in FIG. 6. The results of Comparative Example 2 are illustrated in FIG. 7.

Figure 5:
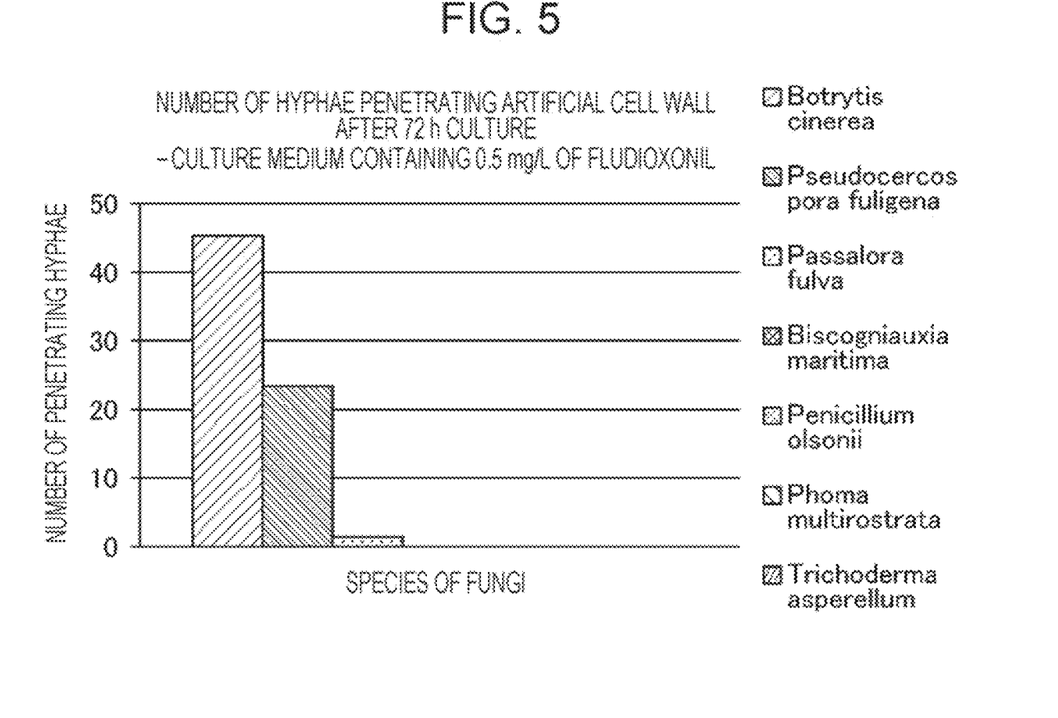
FIG. 5 is a graph illustrating the results of Example 1.
Figure 6:
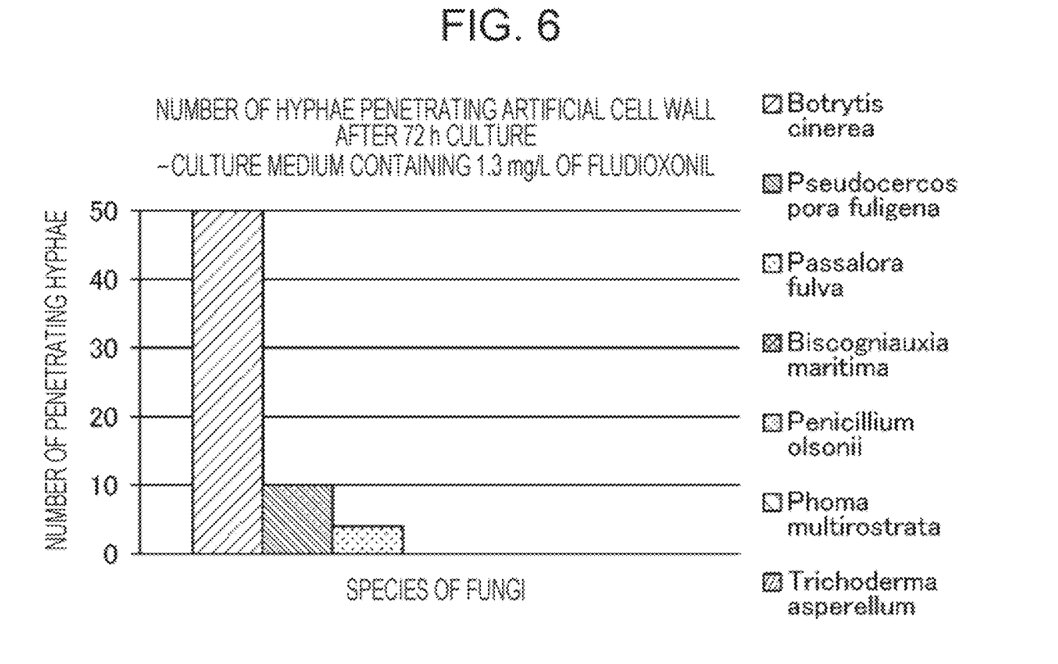
FIG. 6 is a graph illustrating the results of Example 2.

As illustrated in FIGS. 5 and 6, in Example 1 and Example 2 in which fludioxonil was added to the culture solutions so as to have concentrations of 0.5 mg/L and 1.3 mg/L, after the lapse of 72 hours, observation revealed that the tomato pathogenic fungi that are *Botrytis cinerea*, *Pseudocercospora fuligena*, and *Passalora fulva* had hyphae penetrating the artificial cell wall, which is faster than the four species of tomato non-pathogenic fungi that should be excluded from detection (*Biscogniauxia maritima, Penicillium olsonii, Phoma multirostrata*, and *Trichoderma asperellum*). Thus, the tomato pathogenic fungi were selectively detected.

On the other hand, in Comparative Example 1 in which fludioxonil was added to the culture solution so as to have a concentration of 133 mg/L, hyphae penetrating the artificial cell wall were not observed for the four species of tomato non-pathogenic fungi that should be excluded from detection (*Biscogniauxia maritima, Penicillium olsonii, Phoma multirostrata*, and *Trichoderma asperellum*) and the three species of tomato pathogenic fungi that should be detected (*Botrytis cinerea, Pseudocercospora fuligena*, and *Passalora fulva*). Thus, selective detection of the tomato pathogenic fungi was not achieved (not shown). Incidentally, the compound used, fludioxonil, is an agricultural chemical substance; its concentration of 133 mg/L in Comparative Example 1 is a standard concentration at which fludioxonil exerts its agricultural chemical effect.

Figure 7:
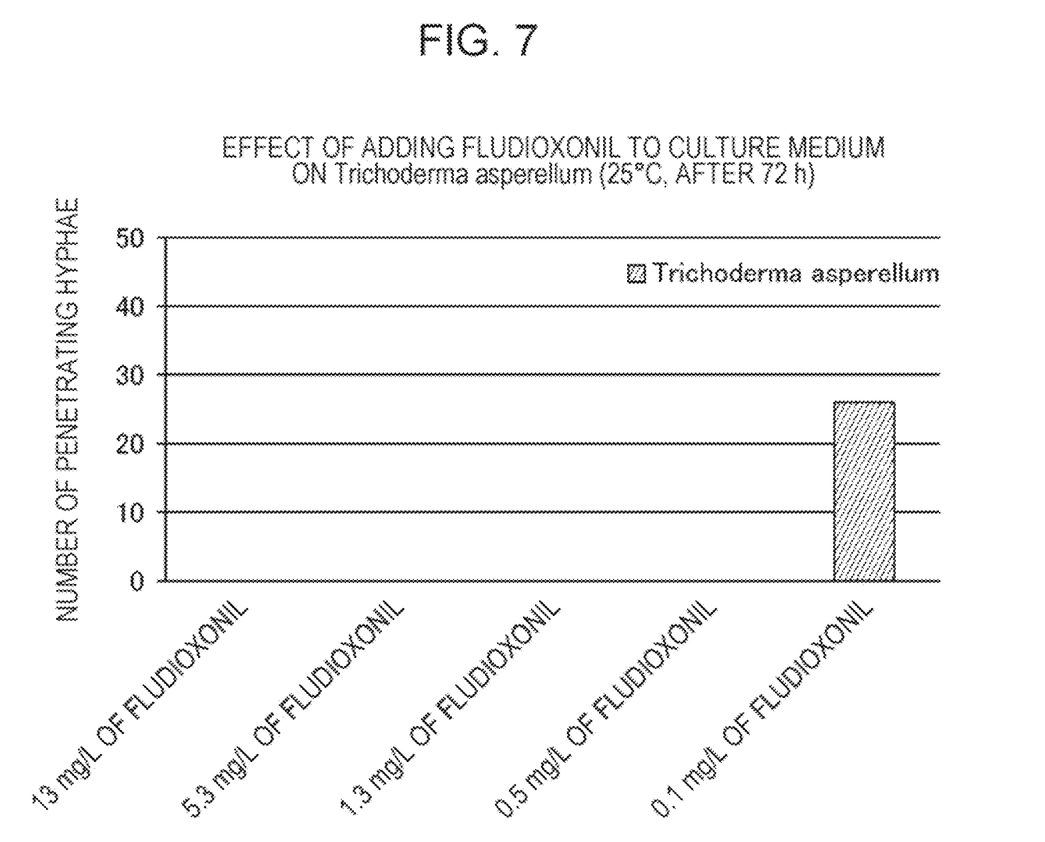
FIG. 7 is a graph illustrating the results of Comparative Example 2.

FIG. 7 illustrates, in Comparative Example 2, the results of the number of hyphae penetrating the artificial cell walls for one species of tomato non-pathogenic fungi that is *Trichoderma asperellum* in the cases where the culture media had the following fludioxonil concentrations: relative to the concentration that provides the agricultural chemical effect, a $1/10$ concentration of 13 mg/L, a $1/25$ concentration of 5.3 mg/L, a $1/100$ concentration of 1.3 mg/L, a $1/250$ concentration of 0.5 mg/L, and a $1/1000$ concentration of 0.1 mg/L. As a result, it has been demonstrated that, even in the case of $1/250$ of the fludioxonil concentration that provides the agricultural chemical effect, growth of *Trichoderma asperellum* is inhibited. However, it has also been demonstrated that, in the case of $1/1000$ of the concentration that provides the agricultural chemical effect, the effect of excluding the one species of tomato non-pathogenic fungi, *Trichoderma asperellum*, is not observed.

Therefore, it has been demonstrated that addition of fludioxonil in the appropriate concentration range to a culture solution enables selective detection of tomato pathogenic fungi.

The device for detecting a tomato pathogenic fungus according to the present disclosure excludes tomato non-pathogenic fungi giving false positives to achieve selective detection of the target tomato pathogenic fungus. Therefore, the detection device according to the present disclosure is suitably applicable to the technical field including elimination of tomato pathogenic fungi adversely affecting tomato and other tomato-related agricultural techniques.

What is claimed is:

1. A method for detecting a tomato pathogenic fungus, the method comprising:
   providing a detection device comprising:
      an artificial cell wall;
      a test-sample-solution receptacle disposed over the artificial cell wall; and
      a culture-solution storage disposed under the artificial cell wall;
   providing a test-sample solution in the test-sample-solution receptacle;
   providing a culture solution in the culture-solution storage, the culture solution containing greater than or equal to 0.5 mg/L and less than or equal to 1.3 mg/L of fludioxonil;
   detecting a tomato pathogenic fungus without detecting tomato non-pathogenic fungi, wherein:
   the test-sample-solution contains the tomato pathogenic fungus and at least one of the tomato non-pathogenic fungi,
   the tomato pathogenic fungus is at least one selected from the group consisting of a tomato gray mold fungus (*Botrytis cinerea*), a tomato *Cercospora* leaf mold fungus (*Pseudocercospora fuligena*), and a tomato leaf mold fungus (*Passalora fulva*), and
   the tomato non-pathogenic fungi include a *Biscogniauxia* fungus, a *Penicillium* fungus, a *Phoma* fungus, and a *Trichoderma* fungus.

* * * * *